(12) United States Patent
Miller (10) Patent No.: US 6,984,527 B2
(45) Date of Patent: Jan. 10, 2006

(54) AUTOMATED QUALITY CONTROL PROTOCOLS IN A MULTI-ANALYZER SYSTEM

(75) Inventor: Kerry Lynn Miller, Elkton, MD (US)

(73) Assignee: Dade Behring Inc., Deerfield, IL (US)

( * ) Notice: Subject to any disclaimer, the term of this patent is extended or adjusted under 35 U.S.C. 154(b) by 73 days.

(21) Appl. No.: 10/638,874

(22) Filed: Aug. 11, 2003

(65) Prior Publication Data

US 2005/0037502 A1    Feb. 17, 2005

(51) Int. Cl.
G01N 1/10    (2006.01)

(52) U.S. Cl. .................. 436/180; 422/99; 422/100; 422/65; 422/67; 436/47; 436/48; 436/49; 436/50

(58) Field of Classification Search .............. 422/65, 422/99–100, 67; 436/47–50, 180
See application file for complete search history.

(56) References Cited

U.S. PATENT DOCUMENTS

| | | | |
|---|---|---|---|
| 4,202,033 A | 5/1980 | Strobel | |
| 4,678,755 A | 7/1987 | Shinohara et al. | 436/43 |
| 5,087,423 A | 2/1992 | Ishibashi | |
| 5,473,551 A | 12/1995 | Sato et al. | 364/496 |
| 5,482,861 A | 1/1996 | Clark et al. | |
| 5,633,166 A | 5/1997 | Westgard et al. | |
| 5,730,939 A | 3/1998 | Kurumada et al. | 422/67 |
| 5,902,549 A | 5/1999 | Mimura et al. | 422/65 |
| 5,937,364 A | 8/1999 | Westgard et al. | |
| 5,941,820 A | 8/1999 | Zimmerman | |
| 5,987,398 A | 11/1999 | Halverson et al. | |
| 6,019,945 A | 2/2000 | Ohishi et al. | 422/65 |
| 6,022,746 A | 2/2000 | Fritchie et al. | |
| 6,027,691 A | 2/2000 | Watts et al. | |
| 6,060,022 A | 5/2000 | Pang et al. | |
| 6,103,193 A | 8/2000 | Iwahashi et al. | |
| 6,117,392 A | 9/2000 | Hanawa et al. | |
| 6,128,544 A | 10/2000 | Ricoux et al. | |
| 6,261,521 B1 | 7/2001 | Mimura et al. | |
| 6,269,276 B1 | 7/2001 | Akhavan et al. | |
| 6,549,876 B1 | 4/2003 | Yundt-Pacheco | |
| 6,581,012 B1 | 6/2003 | Aryev et al. | |
| 6,733,728 B1 * | 5/2004 | Mimura et al. | 422/65 |

* cited by examiner

Primary Examiner—Jill Warden
Assistant Examiner—Jyoti Nagpaul
(74) Attorney, Agent, or Firm—Leland K. Jordan (57) ABSTRACT

A method for automatically operating a sample handling system and associated analyzers to conduct assays on a number of patient samples by comparing the assays to be conducted with a set of assay defined rules, subdividing the analyzers into analyzers which are in compliance with the assay defined rules and analyzers not in compliance with the set of assay defined rules; thereafter, operating the system to supply patient samples to analyzers in compliance or operating the system so as to bring at least one analyzer into compliance with the assay defined rules and supplying patient samples to such an analyzer.

3 Claims, 7 Drawing Sheets

AUTOMATED QUALITY CONTROL PROTOCOLS IN A MULTI-ANALYZER SYSTEM

FIELD OF THE INVENTION

The present invention relates to an automated clinical sample handling worksystem with two or more independent analyzers having samples supplied thereto by an automated conveyor system. More particularly, the present invention relates to a method for automating the processes involved in performing quality control procedures within such an automated clinical sample handling worksystem.

BACKGROUND OF THE INVENTION

Clinical diagnostic analyzers are being developed with increasing levels of complexity and sophistication in order to fully automated the performance of chemical assays and immunoassays of biological fluid samples such as urine, blood serum, plasma, cerebrospinal liquids and the like, these fluid samples almost universally being contained in open or capped sample tubes. Generally, chemical reactions between an analyte in a patient's biological sample and reagents used during performing the assay result in generating various signals that can be measured by the analyzer. From these signals the concentration of the analyte in the sample may be calculated.

A wide variety of automated chemical analyzers are known in the art and are continually being improved to increase analytical menu and throughput, reduce turnaround time, and decrease requisite sample volumes. See for example, U.S. Pat. Nos. 6,103,193, and 6,027,691 and 5,482,861. Such improvements, while necessary in themselves, may be hampered if sufficient corresponding advances are not made in the areas of pre-analytical sample preparation and handling operations like sorting, batch preparation, centrifugation of sample tubes to separate sample constituents, cap removal to facilitate fluid access, and the like.

Analytical throughput may be increased by linking together analyzers of different types, each adapted to perform a certain menu of assays. Another is to link together two or more analyzers of the same type and to allocate incoming samples to whichever analyzer has the smallest backlog of samples to process. Alternately, incoming samples may be allocated between analyzers according to the number and availability of assay resources (reaction vessels, reagents, etc) required by the assay and duplicated on each analyzer.

U.S. Pat. No. 6,261,521 discloses a sample analysis system having a plurality of analyzers placed along a main conveyor line in combination with different types of reagent supply units, such that samples to be tested are assigned to an analyzer having the proper reagent.

U.S. Pat. No. 6,022,746 discloses a method for operating a multi-analyzer system by generating a list of tests to be performed by the system within a given reaction vessel. The list of tests is sorted according to the number of reaction vessels used in performing each test to be performed by the system in a given time period.

U.S. Pat. No. 6,019,945 discloses a transfer mechanism for transferring a sample container holder between a conveyor line and a sampling area formed in each of several analyzers, the transfer mechanism being connectable to each one of the plurality of analyzers. At least two analyzers units are different from one other in either the types of reagent supply means, the number of analysis items that can be analyzed, the number of tests that can be processed in a unit time, or the species of samples to be processed.

U.S. Pat. No. 5,087,423 discloses a plurality of analyzing modules, a plurality of analyzing routes and at least one bypass route bypassing at least one analyzing module are arranged. Each analyzing module is capable of analyzing samples with respect to one or more items, and samples successively supplied from the introduction sides of the modules are selectively delivered into each module.

Although these prior art systems have advanced sample handling and processing throughput, what has not been addressed is the increasing complexity associated with performing the proper quality control procedures within multi-analyzer automated clinical analyzer system. In particular, Laboratory Automation Systems typically have not dealt with the impact of Quality Control procedures on the analytical clinical analyzers they automate. Generally the QC materials are run and analyzed independent of the Automation System. This manual process works OK for a QC regimen that only demands QC on a per shift or per day basis. However, quality control procedures that call for running a calibration or control assay every "n" assays present a significant challenge in a multi-analyzer automated clinical analyzer system. If, for example, four analyzers are each performing ten assays that require a calibration or control assay be conducted every 24 sample assays, the conveyor system linking the analyzers together will become highly concentrated with calibration or control liquids, adversely affecting overall system throughput.

SUMMARY OF THE INVENTION

The present invention provides a method for automating and improving the QC process in an automated laboratory. The laboratory automation will be able to determine exactly when and what QC material needs to be delivered to clinical analyzers and then what action to take when the results from the QC assays have been received. User intervention will only be needed to resolve out of control limit issues. The present invention thus provides a method for automatically operating an sample handling system including a conveyor, analysis pre-treatment devices and analyzers adapted to conduct assays on a number of patient samples, the method by comparing the assays to be conducted with a set of assay defined rules, subdividing the analyzers into a first group of analyzers which are in compliance with the set of assay defined rules and into a second group which are not in compliance with the set of assay defined rules; and then, either operating the sample handling system so as to supply patient samples to analyzers within the first group of analyzers; or, operating the sample handling system so as to bring at least one analyzer within the second group of analyzers into compliance with the assay defined rules and then supplying patient samples to analyzers in the second group.

This new method for operating a sample handling worksystem introduces the capability to:

1) automate the delivery of QC material to clinical analyzers on based on user defined rules related to time or test frequency
2) automatically generate QC LIS test requests based on user defined rules related to material attributes
3) automatically analyze QC results or the purpose of continuing or stopping patient sample processing on clinical analyzers 4) automatically alert a user when QC or Calibration is out of QC or Calibration condition
5) automatically manage expiration of QC material stored on system
6) automatically notify a user when QC material expired or unavailable or one or more clinical analyzers need QC The unique design of an sample tube carrier associated with method for automatically operating an sample handling system the improves its interface with any robotic devices of a clinical laboratory's automated sample handling system and improves the overall reliability of robotic insertion and retrieval of a sample tube from the sample tube carrier.

BRIEF DESCRIPTION OF THE DRAWINGS

For a better understanding of the invention as well as other objects and further features thereof, reference is made to the following detailed description of various preferred embodiments thereof, taken in connection with the accompanying drawings wherein.

DETAILED DESCRIPTION OF THE PREFERRED EMBODIMENTS

Figure 1:
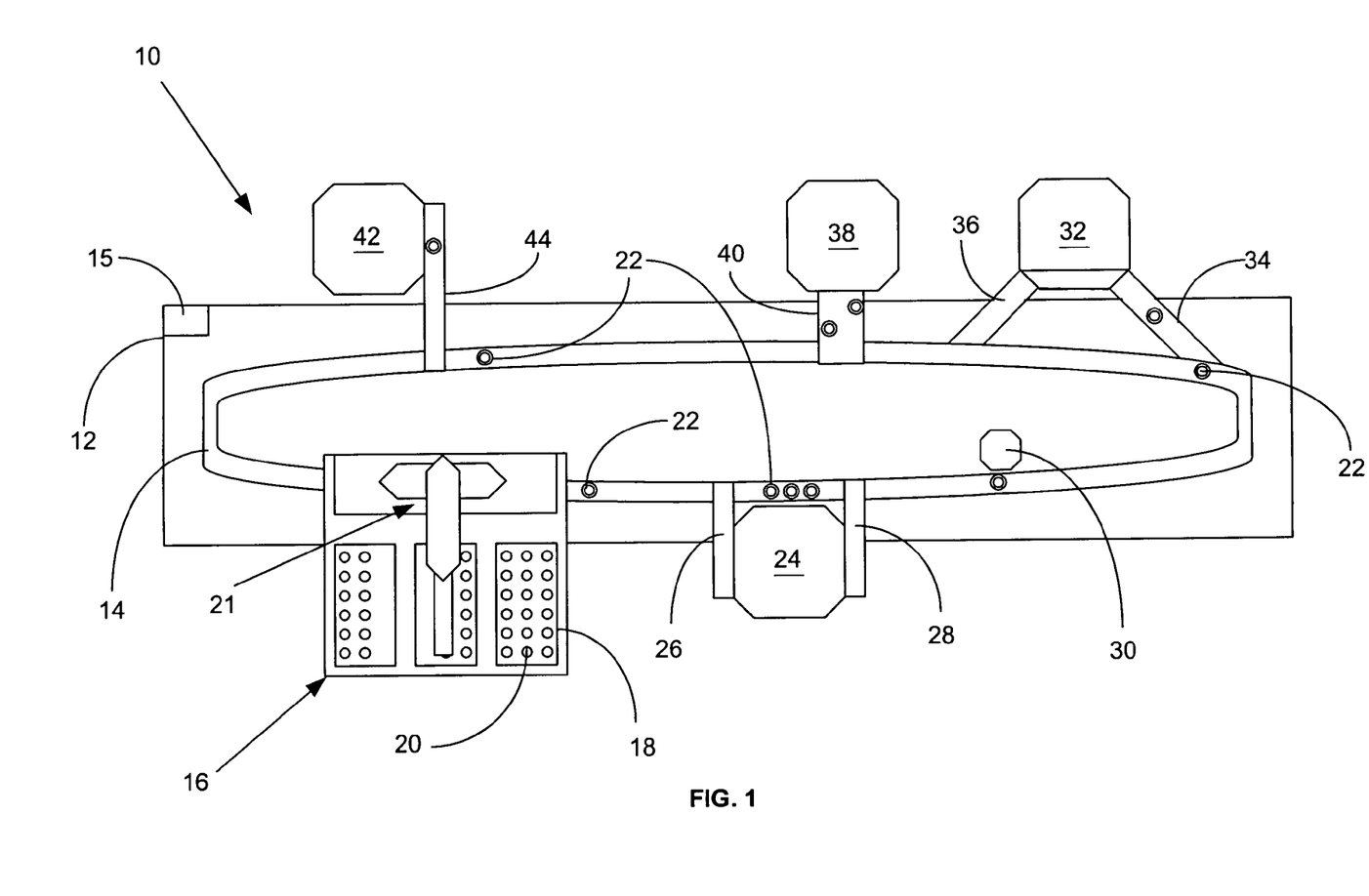
FIG. 1 is a simplified schematic plan view of an automated sample handling system including a conveyor controlled in cooperation with several chemical analysis pre-treatment devices and analyzers in which the present invention may be employed advantageously.

Referring to FIG. 1, there is illustrated an automated clinical chemistry sample handling worksystem 10 capable of automatically pre-processing as necessary multiple sample containers 20, typically sample test tubes, contained in multiple sample racks 18 so as to practice the present inventive method for comparing the assays to be conducted by various analyzers with a set of assay defined rules; subdividing the analyzers into a first group of analyzers which are in compliance with the set of assay defined rules and into a second group which are not in compliance with the set of assay defined rules; and then, either operating the sample handling system so as to supply patient samples to analyzers within the first group of analyzers; or, operating the sample handling system so as to bring at least one analyzer within the second group of analyzers into compliance with the assay defined rules and then supplying patient samples to analyzers in the second group. Typically, specimens to be automatically processed are provided to sample handling system 10 in multiple containers, such as test tubes, which can be capped. Each of the sample containers 20 is provided with container identification indicia, such as a bar code, indicating a patient's identification as well as optionally the assay procedures to be accomplished upon the sample therein. The containers are generally held in one or more holders such as racks that may have additional identification indicia thereon.

The sample handling worksystem 10 comprises an operating base 12 on which a belt-like conveyor track 14 transports a plurality of individual sample tube containers 20 carried in sample tube carriers 22 from a sample tube loading/unloading station 16 to an automated centrifuge 24 to an automated tube de-capper 30 for automatically removing caps from capped sample containers 20 and to one or more conventional clinical analyzers 32, 38, and 42 before returning each sample container 20 to the sample tube loading/unloading robotic station 16. It will be understood that more than three analyzers 32, 38, and 42 may be linked by conveyor track 14, but for purposes of simplicity, only three are shown. The sample handling worksystem 10 has a number of sensors, not illustrated, for detecting the location of a sample tube container 20 by means of identifying indicia placed on or within each sample tube carrier 22. Conventional bar-code readers may be employed in such tracking operations.

Centrifuge 24 and each analyzer 38, 42 and 32 are generally equipped with various robotic mechanisms 26 and 28, 40 and 44 or tracks 34 and 36, respectively, for removing a sample tube carrier 22 from track 14, moving the sample tube carrier 22 to and from centrifuge 24, to and from or into and out from analyzers 38, 42 and 32, respectively. Typically, the loading/unloading station 16 includes at least two X-Y-Z robotic arms 21 conventionally equipped with clamping robotic hands.

The sample handling worksystem 10 is controlled by a conventional computer 15 preferably a microprocessor based central processing unit CPU 15 housed as part of or separate from the system 10 to move the sample tube carrier 22 to each operating station 24, 30, 32, 38, 42 and 16 whereat various types of assay processing occurs, as described below. CPU 15 controls sample handling system 10 according to software, firmware, or hardware commands or circuits like those used on the Dimension® clinical chemistry analyzer sold by Dade Behring Inc. of Deerfield, Ill., and are typical of those skilled in the art of computer-based electromechanical control programming.

Figure 2:
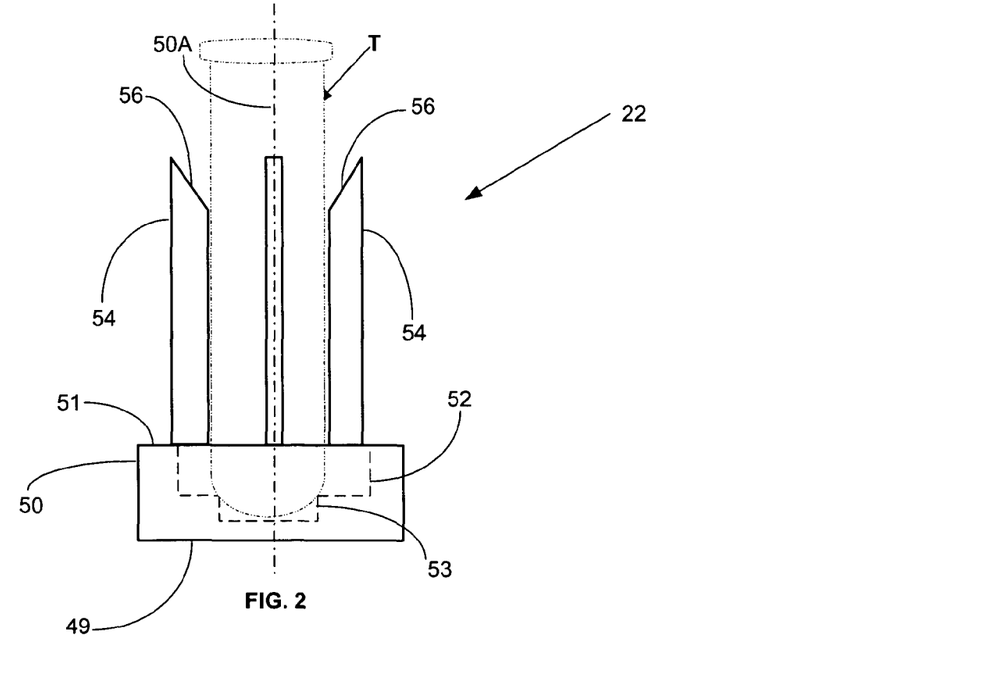
FIGS. 2 and 2A are simplified elevation and plan views of a sample tube carrier adapted for use in the sample handling system of FIG. 1.

FIG. 2 is an elevation view of a first embodiment of the sample tube carrier 22 for transporting a cylindrical sample tube T shown in phantom lines having a tube diameter and a tube longitudinal height, the carrier comprising a generally cylindrical carrier body 50 having a central axis 50A and a cylindrical hole 52 formed along said axis depending from a top surface 51 of the carrier body 50 towards a bottom surface 49 of the carrier body 50. An optional recess 53 centered along axis 50A may be seen, recess 53 provided to accommodate the rounded bottom typically found on clinical sample tubes T.

Figure 2A:
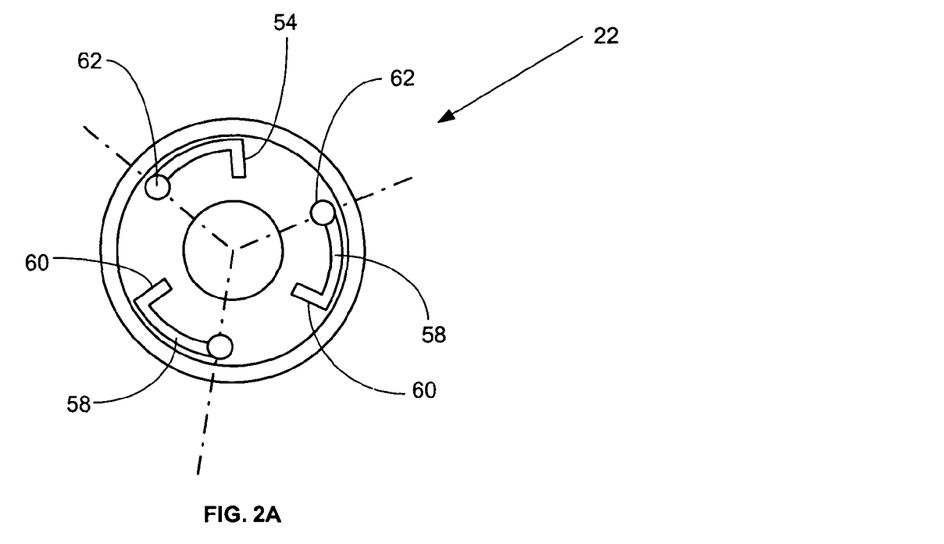
Figure 3:
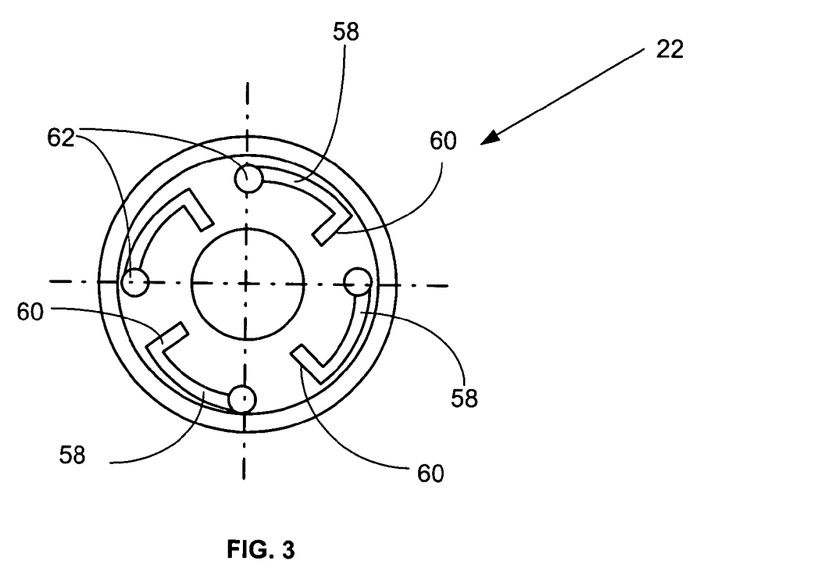
FIGS. 3 and 3A are simplified plan views of an alternate embodiment of a sample tube carrier adapted for use in the sample handling system of FIG. 1.
Figure 3A:
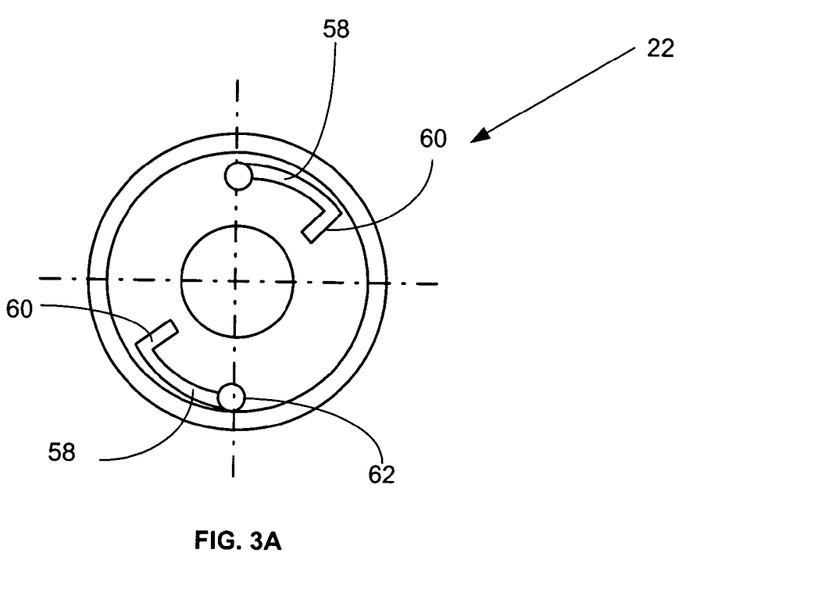

An important feature of carrier 50 is at least two vertically oriented arms 54 symmetrically disposed within the cylindrical hole 52 and extending a given distance upwards above the top surface 51. The at least two vertically oriented arms 54 include an tapered upper end 56 seen tapered downwardly towards the central axis 50A. Three of such vertically oriented arms 54 are seen in FIGS. 2 and 2A; FIG. 3 illustrates an alternate embodiment having four vertically oriented arms 54 and FIG. 3A illustrates another alternate embodiment having two vertically oriented arms 54.

FIG. 2A shows each of the at least two vertically oriented arms further including a lever portion 58 attached at a bottom end thereof, each lever portion 58 mounted on pins 62 having a finger portion 60 and adapted to cooperate with an automatic tube aligning mechanism described hereinafter in conjunction with FIGS. 5 and 5A.

Figure 4:
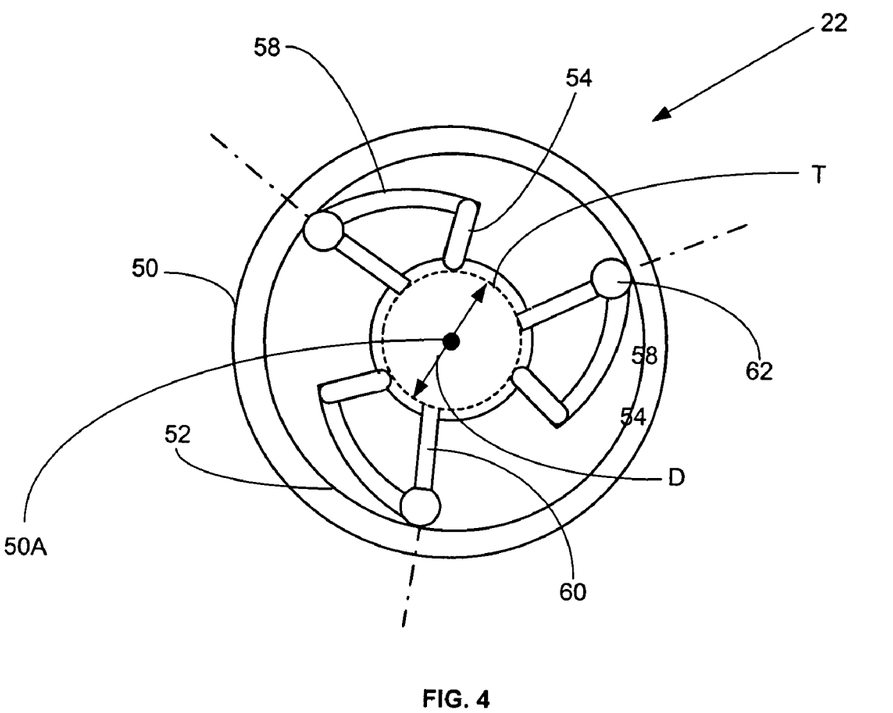
FIGS. 4 and 4A are enlarged plan views illustrating an important feature of the sample carrier of FIG. 2.
Figure 4A:
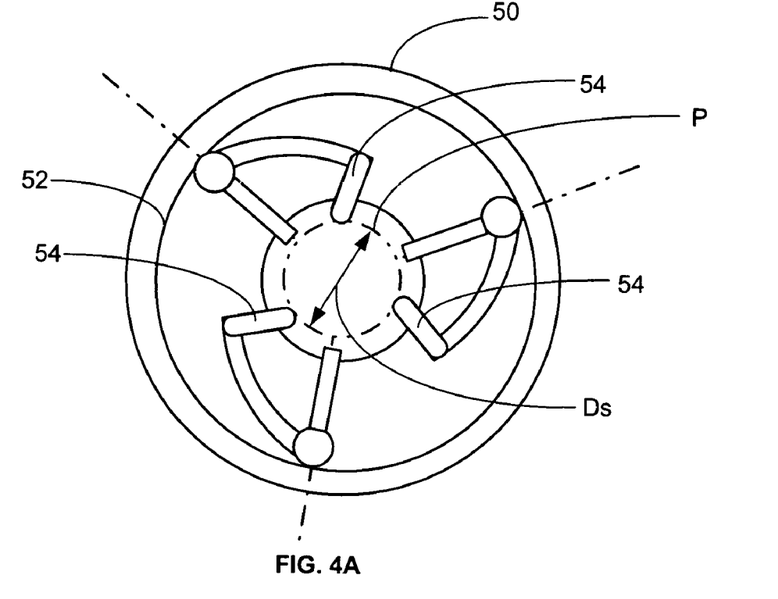

FIGS. 4 and 4A are presented in a simplified form in order to clearly illustrate another feature of carrier 22. In both FIGS. 4 and 4A, three dot-dash lines emanate from the center of carrier 22 and are equally distributed around central axis 50A. FIG. 4 is a simplified illustration of a "loaded" state of carrier 22 in which a phantom sample tube T drawn in dashed lines and having a diameter D is positioned between the at least two vertically oriented arms 54. In this state, lever portions 58 are rotated around pins 62 so that arms 54 are disposed along a circular path P having diameter equal to the tube diameter D. Preferably the at least two vertically oriented arms 54 extend a distance upwards above the top surface 52 at least as large as one-half the longitudinal height of tube T, so that, as may be seen in conjunction with FIG. 2, the present invention causes a perfectly vertical orientation of sample tube T held in contact with the at least two vertically oriented arms 54.

Specifically, FIG. 4A is a simplified illustration of an "unloaded" state of carrier 22 in which the at least two vertically oriented arms 54 rotated around pin 62 so that the arms 54 are disposed along a circular path Ps shown in dot-dashed lines and having a diameter Ds smaller than the tube diameter D. This position of arms 54 defines an "unloaded" state of carrier 22 in which sample tube T is not carried by carrier 22. As described earlier, during operation of the sample handling system 10, sample tube loading/unloading robotic station 16, as well as robotic mechanisms 26 and 28, 40 and 44, will move a sample tube T to and from sample tube racks 18, to and from centrifuge 24 or into and out of analyzers 38, 42 and 32. Whenever a carrier 22 is not carrying a sample tube T, the at least two vertically oriented arms 54 are automatically moved to the circular path P by a spring-activated mechanism 70 seen in FIG. 5 operable in a first activated state to symmetrically urge the arms 54 towards the central axis with a first force so that the at least two vertically oriented arms 54 are automatically symmetrically rotated around pin 62 causing arms 54 to be symmetrically disposed along circular path Ps in the "unloaded" state of carrier 22.

The spring-activated mechanism 70 comprises a rotatable circular button 72 disposed at a bottom of the closed cylindrical hole 52, a spring 74 with a first extended spring length and attached at a first end to a projection 75 of the circular button 72, the spring 74 being further wrapped along an exterior surface of the circular button 72 with a first extended length and attached at a second end to a pin 78 integral with the bottom of the closed cylindrical hole 52.

Figure 5:
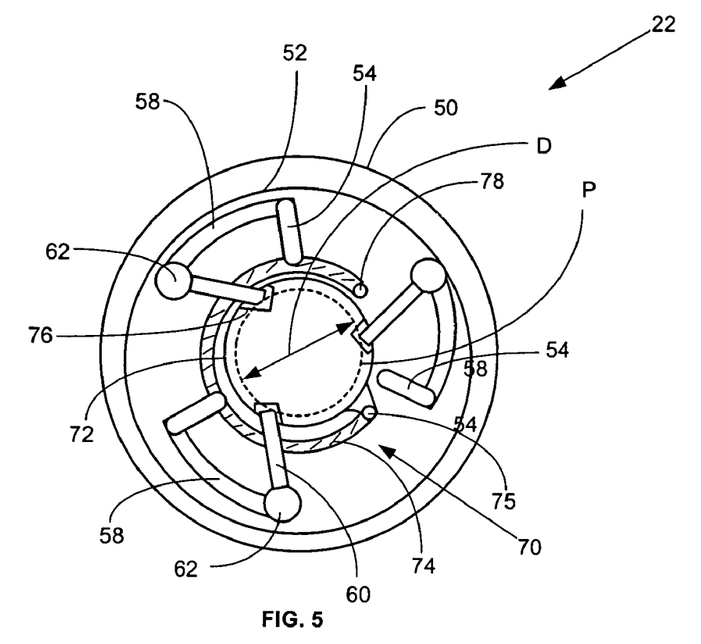
FIGS. 5 and 5A are enlarged plan views illustrating another important feature of the sample carrier of FIG. 2.
Figure 5A:
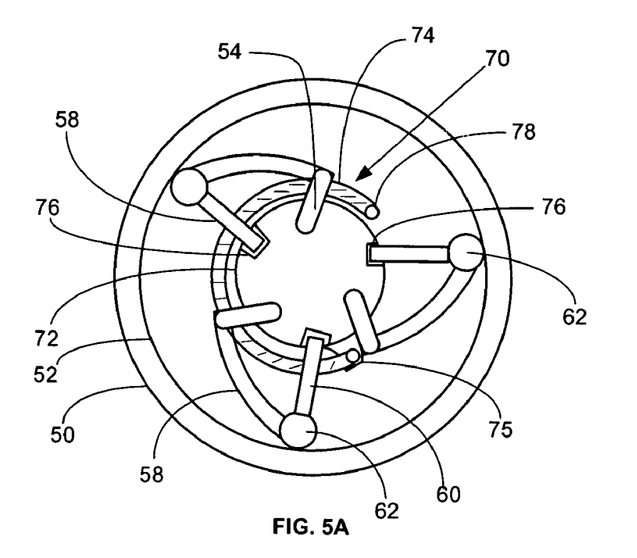

FIG. 5 further illustrates at least two notches 76 formed in the circular button 72, notches 76 sized and shaped to loosely accept the finger portion 60 of the lever portion 58 of each of the at least two vertically oriented arms 54 so that the finger portions 60 are able to remain in notches 76 when button 72 is rotated between the "loaded" state of carrier 22 seen in FIG. 5 and an "unloaded" state of carrier 22 seen in FIG. 5A.

FIG. 5 illustrates the "loaded" state of carrier 22 wherein the spring-activated mechanism 70 is in a second activated state to urge the arms towards the central axis with a second force when circular button 72 is rotated, the spring 74 having a second extended spring length and the at least two vertically oriented arms being disposed along a circular path P having the same diameter D as the tube diameter D. In particular, the first extended length is shorter than the second extended length so that as a tube T is inserted by any sort of a robotic tube handling mechanism between the at least two vertically oriented arms 54, then the at least two vertically oriented arms 54 are moved symmetrically outwards as in the "loaded state" of FIG. 5, thereby relaxing spring 74 to the second extended length and generating a corresponding symmetrically inwardly directed tube grasping force. As described previously, the upper end 56 of each of the at least two vertically oriented arms 54 is tapered downwardly to facilitate loading of a tube T. Importantly, the symmetrically positioned at least two vertically oriented arms 54 and the symmetrically generated tube grasping force automatically position tube T in the geometric center of carrier 22.

A close comparison of FIGS. 5 and 5A shows that with the features described above, when a tube T is inserted between the at least two vertically oriented arms 54, tube T slides downwards along the taper of upper ends 56 of arms 54 forcing the arms 54 outwards. Outward movement of arms 54 causes the lever portion 58 to rotate counterclockwise around pin 62. Counterclockwise movement of lever portion 58 in turn causes finger portion 60 and located within notch 76 to move in a direction that rotates button 72 clockwise. Clockwise rotation of button 72 shortens the length of spring 74 to the second extended length; importantly, the length and tension properties of spring 74 are selected so that even when spring 74 is stretched at this shortened second extended length, spring-activated mechanism 70 continues to urge arms 54 towards the central axis 50A with force sufficient to maintain tube T in a true vertical orientation. Since each one of the at least two vertically oriented arms 54 has its finger portion 60 of lever portion 58 located within a notch 76 of button 72, when button 72 is rotated by insertion of tube T between arms 54 as described, arms 54 will be uniformly displaced outwards from the path P seen in FIG. 4A to the path T seen in FIG. 4, thereby automatically causing tube T to be positioned at the geometric center of carrier 22.

The present invention may be implemented using a computer interface module CIM that allows for a user to easily and quickly access a variety of control screens and status information display screens that fully describe a plurality of interrelated automated devices used for sample preparation and clinical analysis of a patient's biological sample. Such a CIM preferably employs a first information display screen that is directly linked to a plurality of additional information display screens containing on-line information about the operational status of plurality of interrelated automated devices as well as information describing the location of any specific sample and the status of clinical tests to be performed on the sample. The CIM is thus adapted to facilitate interactions between an operator and automated clinical analytical system 10 wherein the module comprises a visual touch screen adapted to display a menu including icons, scroll bars, boxes and buttons through which the operator may interface with the clinical analytical system and wherein the menu comprises a number of function buttons programmed to display functional aspects of the clinical analytical system. The computer interface further comprises a number of function specific buttons programmed to display detailed functional aspects for each function button so that additional information about the status and performance of the clinical analytical system may be displayed by activating no more than two of said function buttons and function specific buttons. The design of the CIM and its interface with a clinical laboratory's patient and operating database allows an operator to access nearly all important information screens using such a flat menu wherein only two screens are activated whereby the need for a simple and rapid method to easily display information defining the overall status of the analytical system is achieved.

Figure 6:
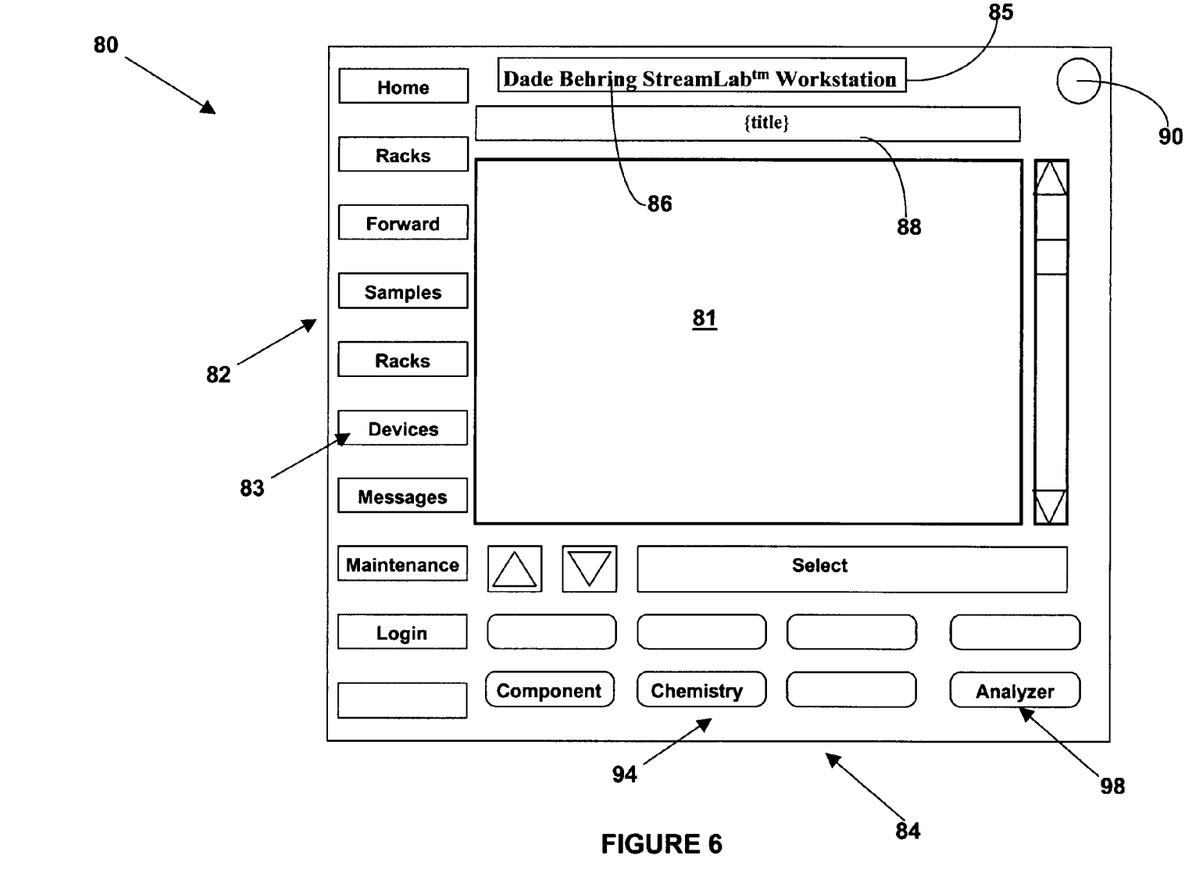
FIG. 6 is a typical representation of a computer interface module information display screen useful in practicing the present invention; and, FIG. 7 is a plan view of the automated sample handling system of FIG. 1 illustrating an example of the present invention.

FIG. 6 shows a computer interface display or module CIM 80 useful in practicing the present invention. In a particularly useful embodiment, like described in U.S. Pat. No. 6,442,440 and assigned to the assignee of the present application, CIM 80 comprises a visual touch screen 82 for user input and information display displaying a number of icons, scroll bars, boxes or buttons through which an operator may interface with the clinical system 10 and a conventional Laboratory Information System (LIS) to interrogate or supply patient and operational data. Touch screens like the ones employed in CIM 80 are commercially available and their operation and interconnection with the other devices including CPU 15 and a hospital's LIS are known in the art. Several well known terms in the art are used to indicate an interaction between an operator or technician and CIM 80; phrases such as "activating a button", "pressing a button", "touching a button" are generally intended to indicate any of several methods to select an given area of the display or screen portion of CIM 80. To insure a consistent interface all screens should share some common attributes including scrolled area 81 to present detailed information about each of the buttons 82 or 84 described hereinafter, a title bar 85 that indicates the system name 86 (for example, "Dade Behring StreamLab® Workstation"), and the screen title 88 of the specific screen being displayed. The location of the Title Bar 85 is at the top and center of the CIM 80. Each screen in CIM 80 also includes has provisions for function specific buttons 84 that are specific to the screen being displayed. As described in the above mentioned U.S. Patent, an analyzer status icon/button 90 is provided to indicate the overall status of each of the clinical analyzers 32, 38, and 42.

The general function buttons 82 provide the user with express navigation controls and are shown as located from top to bottom along the left edge of CIM 80 and are named to indicate their function. The function specific buttons 84 include a Chemistry button 94 to provide the status of the reagent inventory including assay reagents and calibration or control compositions on each of the clinical analyzers 32, 38, and 42. The general function buttons 82 includes a device panel button 83 which indicates the status of the various sample-preparation devices like the loading/unloading station 16, automated centrifuge 24, tube de-capper 30 as may be required for the different sample preparation operations such as decapping of a closed sample tube, aliquotting of portions of samples from a primary tube to a secondary tube, sample identification, dilution, centrifugation, etc, in order to prepare the original biological sample for analysis by any of the clinical analyzers 32, 38, and 42. An Analyzer Configuration screen may be accessed by selecting an Analyzer button 98 from among the group of function specific buttons 84 to display the operating configuration details of a specific one of the analyzers 32, 38, and 42, such as assay menu, reagent inventories, calibration and control readings, incubation temperatures, throughput, etc. In addition, Chemistry Configuration Selection information concerning assay and reagent operating configuration details associated with a specific assay may be readily accessed by selecting a Chemistry button 94 from among the group of function specific buttons 84.

Calibration of analyzers 32, 38, and 42 involves defining a mathematical relationship between the concentration of the analytes of interest and the detection signals generated. These relationships in immunoassays are commonly non-linear such that calibration of an analyzer requires multiple standard solutions to define the signal-analyte relationship.

A standard or calibration or control solution is a solution of various ingredients especially prepared to exhibit extended stability and preferably being capable of simultaneous use in methods for determination of multiple analyte-related analytes. Such solutions typically contain serum albumin as a protein component serving as an acceptable binding reservoir for certain analytes and as an acceptable stabilizing milieu for others. Serum albumin is useful in a range between 40 g/L and 80 g/L which mimics the physiologic protein concentration of serum. Likewise, to mimic the ionic environment in serum, NaCl is added in a range between 100 and 200 mmoles/L solution. The amount of NaCl may vary depending on the sensitivity of the analytical system to ionic strength. If the analytical system is insensitive to ionic strength, NaCl addition may not be required. Likewise, to enhance the buffering capacity of the calibration solution, buffers which maintain pH in a range between 6.0 to 8.0 may be required. An example of such a buffer is HEPES (N-2-hydroxyethyl!piperazine-N'-2-ethane-sulfonic). If the analytical system is insensitive to pH, the protein component of the matrix may supply all the buffering capacity that is required.

Subsequent to addition of protein, salt, and buffer, agents active against contaminating microbes are included in calibration solutions to achieve a desired amount of stabilization. These agents may consist of any number of compounds which are effective against bacteria and fungi, are inert in the analytical system, and are unreactive towards components of the matrix of the calibration solution and the specific analytes contained therein. In a typical embodiment, Polymyxin B, is added at a concentration of 0.02 g/L along with sodium pyrithione at a concentration of 0.2 g/L. At these concentrations, Polymyxin B is active mainly against bacteria and sodium pyrithione is active primarily against fungi. It is also useful to add a broad spectrum anti-microbial agent to reinforce the activities of the others. This particular combination of agents is known to be effective in providing a sterile environment for the calibration solutions for an extended period of six months or more as discussed hereinafter.

Subsequent to the preparation of the base matrix, in the instance of calibration solutions, the specific analytes of interest are added in ranges which cover about 105% of the physiologically relevant concentrations found in human serum. Exemplary control solutions are prepared with analyte content of 0% and 105%.

Control and operation of the sample handling worksystem 10 by CPU 15 is based on a number of assumptions and definitions as follows.

Precision QC materials are calibration and control compositions having known levels of a variety of analytes in a stable base matrix and for which the measurements made are made without deviation. Precision QC materials are calibration and control compositions that have been carefully prepared as described above outside the domain of sample handling worksystem 10 under strict production and testing processes so as to provide precise levels of a variety of analytes in a stable base matrix. Such materials are validated for precision generally having the analyte(s) measured repeatedly within ±5% of the same value, not necessarily the concentration value provided on the label of the calibration and control composition container. With Precision QC materials, accuracy can be obtained by applying the appropriate offset. Precision QC materials are assigned time periods for which each of the analytes is known to be stable. Validation must be completed prior to introducing Precision QC materials onto sample handling worksystem 10. The following elements of validation are assumed:
1. Specimen analysis on a minimum of twenty different working days;
2. Collect data from candidate control specimen analysis;
3. Compute mean and standard deviation; and,
4. Acceptance criteria
   Coefficient of variation below established limits
   Meet medical requirements The analysis of the Precision QC materials will consider the following:
1. Only uses validated Precision Control specimens.
2. Analyze Precision Control specimen each Run or Run Segment:
3. The shortest run is one assay; the longest run covers one work shift.
4. Long runs are divided into segments comprising 10 to 20 specimens.
5. Each analyte is managed independently.
6. Each clinical analyzers 32, 38, and 42 is managed independently.
7. Acceptance Criteria:
   Most recent result less than three times the standard deviation from the arithmetic mean.
   Seven most recent results not all above arithmetic mean.
   Seven most recent results not all below arithmetic mean.
   Seven most recent results do not show an upward trend.
   Seven most recent results do not show a downward trend.

Accuracy QC materials are calibration and control compositions that have been carefully prepared as described above outside the domain of sample handling worksystem 10 under strict production and testing processes so as to provide precise levels of a variety of analytes in a stable base matrix. Such materials are validated for precision generally within having the analyte(s) concentration within ±5% of label value, a concentration value provided on the label of the calibration and control composition container. Accuracy QC materials are assigned time periods for which each of the analytes is known to be stable. Validation per the following criteria must be completed prior to introducing Accuracy QC materials onto sample handling worksystem 10.
1. Only validated Accuracy Control specimens are used.
2. Analysis should be done every four runs, for example, although this is a configurable frequency for the domain 1 to x runs.
3. Each analyte is managed independently.
4. Each clinical analyzers 32, 38, and 42 is managed independently.
5. Acceptance Criteria performed on LIS.

The method of operating the sample handling worksystem 10 according to the present invention employs computer programs within CPU 15 using conventional control and operation sub-routines employing:
1. User Defined Operations
2. System Defined Operations
3. Analyzer Operational Status
4. Assay Defined Rules
   to automatically perform the following operational procedures:
1. Schedule delivery of Precision Control material at a specified interval for each clinical analyzers 32, 38, and 42, for each analyte and each run/run segment.
2. Send QC specimens to appropriate analyzers as needed.
3. Generate LIS request for relevant QC analysis.
4. Operate the Analyzers to produce QC results.
5. Report all QC results to LIS (for both sample handling worksystem 10 and LIS generated requests)
6. Apply Precision Control acceptance criteria to enable continued analysis of a specified assay on a given analyzer.
7. Allow a user to override rejection of Precision Control result.
8. Allow a user to rerun or arbitrarily schedule a Precision Control analysis for any analyte or clinical analyzers 32, 38, and 42.
9. Require pass/fail user entry of Accuracy Control results (as obtained from LIS).
10. Prevent delivery of patient samples to analyzers with expired QC. QC expires when required QC analysis has not been performed or acceptance criteria not met. All analytes in a patient test request must have a corresponding current accepted QC.
11. Prompt an operator to load QC when viable material is not resident on sample handling worksystem 10.
12. Prevent use of a Precision Control material that has been resident on the sample handling worksystem 10 longer than a user defined time period.
13. Allow User to enter Precision Control parameters, including, Mean, Standard Deviation, Precision control specimen Ids, Acceptance limits, and the like.
14. Display current QC expiration (counts or time) for each analyte and clinical analyzer 32, 38, and 42.
15. Store in memory the last thirty days of QC results.

The following operational examples describe how a user might interact with the CAL/QC subsystem of sample handling worksystem 10 and how sample handling worksystem 10 could be automatically operated in various situations when controlled by the operational method disclosed herein. The term "CAL/QC" denotes either a Calibration or a Quality Control event in which Calibration materials or Control material are employed.

User Defined Operations
1. User Configures Sample Handling Worksystem 10 CAL/QC
   Before the system can perform any CAL/QC functions all setup and configuration must be complete. The setup and configuration consists of identifying the QC materials, specifying the QC rules & selecting the desired system behavior.
2. User Identifies QC Material
   All QC material the system must automatically recognize needs to be identified in advance by entering the QC Material Name, Lot Number, and Barcode ID for both Precision QC materials and Accuracy QC materials.
3. User Selects which Tests are Run on QC Material
   Part of the QC material identification is to indicate which tests are associated with the material and how long those materials can be used by entering the Test ID, QC Material Name, Mean and Standard Deviation, and Viability Timeout (how long can QC be on system until it cannot be used).
4. User Specifies QC Scheduling Rules
   The system behavior toward QC is configurable by the user to match their local practices. QC can be performed on a time interval by entering the minimum time and the maximum time a QC material is validated for. QC can be performed on a count basis by entering the minimum count and the maximum count a QC material is validated for.
5. User Specifies QC Acceptance Rules
   How the QC results are accepted/rejected are also user configurable. The QC result can be automatically or manually accepted or rejected. QC acceptance or rejection by the system is only used to drive system behavior. The sample handling worksystem 10 does not provide a full laboratory QC package.

Precision QC Acceptance is accomplished whenever a Precision QC has been Run or when a predefined set of Acceptance Rules are met. Typical Acceptance Rules include:
  a) QC range comparison in which alternatives like QC result less than 3 SDs from Mean or QC results within High/Low limits are met.
  b) Last 7 QC results not all above or below Mean
  c) Last 7 QC results not indicating a negative or positive trend
  d) Accept/Reject on User Input 6. User Specifies Sample Handling Worksystem 10 QC Actions Based on system conditions and QC results the system can behave in a number of ways. The configuration selections determine this behavior. This system behavior centers on displaying warnings and/or disrupting sample flow to analyzers that do not achieve QC acceptance.

If Precision QC is not available, when is it due to be received? (Warning or No Warning)

If Precision QC is not available, when is it due to be received? [Stop routing samples to Clinical analyzers 32, 38, and 42 or Continue routing samples to clinical analyzers If Precision QC is rejected? [Stop routing samples to Clinical analyzers 32, 38, and 42, or Continue routing samples to Clinical analyzers 32, 38, and 42]

If multiple QC levels are not available, when are they due to be received? (Run All Levels or Run One Level)

7. User Specifies Calibration Setup

The calibration support feature allows the user to define calibration intervals and monitor when calibrations are coming due. The system monitors the LIS data from the clinical analyzers 32, 38, and 42s for calibration results. When a calibration result is received the calibration time is reset to zero. The sample handling worksystem 10 does alerts the user that a calibration result for a method has not been received within the defined time.

A user enters calibration frequencies for all configured tests by entering a Min Time defined as a timeout for warning that calibration is coming due, and by entering a Max Time defined as a timeout for warning that calibration is overdue (expired).

A user also enters Calibration Actions for the sample handling worksystem 10 and these are generally cover:

If Calibration is past Min Time and is therefore soon due, then either a Warning or No Warning signal may be issued.

If Calibration is past Max Time and is therefore overdue, then either a Warning or No Warning signal may be issued.

8. User Specifies QC Material Storage Location

All QC materials are stored together in a user designated lane when the QC material is not in use. The Maintenance/Setup/Input Output Module lane assignments screen is used to select the QC storage lane. A lane assigned as a QC Output lane will act similar to an Output only lane. This lane, however will only accept QC materials for storage.

9. User Puts Precision QC Material on Sample Handling Worksystem 10

All QC material should be placed on the sample handling worksystem 10 via the Priority Input lanes. After the barcode ID is read the sample handling worksystem 10 will either send the QC material directly to clinical analyzers 32, 38, and 42s or place the QC material in the QC rack.

If the Precision QC material entered the sample handling worksystem 10 via a routine rack, the system considers the QC material was entered when the rack was inserted. To ensure maximum use of QC material before its viability limits are exceeded, users should be encouraged to use one of the Priority Input racks instead.

The following situations may exist:
  a) Precision QC status Normal, Pending or Overriden, and this exists if all tests associated with the Precision QC material have a status defined above, the QC material will be stored on a QC rack.
  b) Precision QC status Warning, Error or Rejected, and this exists if any tests associated with the Precision QC Material have a status defined above, the QC material will be immediately delivered to any clinical analyzers 32, 38, and 42 requiring QC.
  c) Precision QC material ID duplicated, and this exists if a user possibly puts on a new tube with Precision QC material before removing the corresponding "old" material.
  d) "Duplicate" replacing not expired material, and this exists if the old precision QC material is still viable it will have to be sent to the Priority Output rack for discard. After the "old" material has been sent to the Priority Output rack the "new" material will be accepted by the system. Although the system keeps constant track of where samples are, to guarantee there is no possibility of a mix-up duplicate ID's are not allowed. Once a sample tube is put in the Priority Output rack it will not be placed back on the track. As a result a sample ID that duplicates an ID in the Priority Output rack would not be considered a "duplicate".
  e) "Duplicate" replacing expired material, and this exists if, the old material was already expired and in the Priority Output rack the new material will be accepted normally.

10. User Removes Precision QC Material from Sample Handling Worksystem

All Precision QC materials should be removed via the Priority Output lanes when either of the following two situations exist:
  a) When all tests associate with a Precision QC Sample have expired, the work cell will automatically place the QC material in the active Priority Output lane.
  b) If a user wants to remove a Precision QC material that has not expired they need to explicitly request it to be delivered to the active Priority Output lane (via the CAL/QC status screen).

Precision QC material has an expiration time at which time it is no longer considered viable. Each test associated with a given QC material can have a separate timeout. This is done to recognize the possible varying degradation rates between analytes in the Precision QC material. Either of the following two situations may exist:
  a) Full expiration: when all associated tests for a given Precision QC expire, the QC material will be no longer be used to perform QC. The expired QC material container will be placed in the active Priority Output lane for user disposal.

b) Partial Expiration: When a Precision QC expires for a given test it can no longer be used to QC that particular test. As long as at least one test is viable the sample handling worksystem 10 will retain the QC material in the QC rack.

11. User Overrides Precision QC Status

The user can override any rejection of a QC result (automatic or manual). When the user overrides a rejected QC result the sample handling worksystem 10 will show an override status until another Precision QC material is run. The result of that will then replace the override status. While a QC result is overridden the sample handling worksystem 10 will schedule patient samples normally (treated the same as Normal or Warning status).

12. User Reruns Precision QC

The user can rerun a Precision QC at any time. When the result of the rerun is received it will treated as if it were the next normally scheduled QC. The status determined by this QC result will supercede the current status.

13. User Reviews Precision QC Status

The user can review the status of all Precision QC material on the sample handling worksystem 10 via the CAL/QC Status screen.

14. User Reviews Calibration Status

The user can review the status of all clinical analyzers 32, 38, and 42 Calibrations in the sample handling worksystem 10 via the CAL/QC Status screen.

15. User Calibrates Clinical Analyzers 32, 38, and 42

The user can calibrate and re-calibrate the clinical analyzers 32, 38, and 42 at any interval. Calibration can only be done at the clinical analyzers 32, 38, and 42. The sample handling worksystem 10 support for calibration is available only for scheduling convenience and management.

Whenever a calibration is obtained on an analyzer, the analyzer sends a "Calibration Result Message" to CPU 15. The data in this message will be accepted and stored by the sample handling worksystem 10 and utilized for the purposes of managing and supporting clinical analyzers 32, 38, and 42 calibration via the sample handling worksystem 10.

16. User Runs Precision QC on Clinical Analyzers 32, 38, and 42

The user can run Precision QC directly on the clinical analyzers 32, 38, and 42 at any time. The sample handling worksystem 10 will recognize the QC result as if it had scheduled and delivered the QC itself. If the user enters the Precision QC material ID in response to an LIS query, the sample handling worksystem 10 will respond with all tests appropriate for that particular clinical analyzer 32, 38, or 42 (i.e. status of Warning, Rejected or Override and configured for the clinical analyzers 32, 38, and 42). Alternately, the user can enter the Precision QC material ID and select the tests to be run.

17. User Unlocks QC Rack

If the user tries to unlock the QC rack a confirmation popup will be displayed to confirm this user action. If "continue" is pressed the rack will be unlocked. If the rack is removed all QC material in the rack will be lost. If the system needs to retrieve QC material from an unlocked rack or place QC material in available space on an unlocked rack, the rack will be relocked and used normally. Once relocked the user will have to make a new request to unlock the rack.

System Defined Operations

The following operational examples describe System Defined Operations that might be integrated into sample handling worksystem 10 so that the sample handling worksystem 10 could be automatically operated in various situations when controlled by the operational method disclosed herein.

1. Sample Handling Worksystem 10 Schedules Precision QC on Clinical Analyzers 32, 38, and 42

The sample handling worksystem 10 will schedule a Precision QC material delivery to an clinical analyzers 32, 38, and 42 to coincide with the QC frequency established by the setup screens. If count is the method defined, the QC material will be delivered when the maximum count is reached. A test that has reached its minimum limit will have its QC scheduled also if the same QC material is being delivered to the clinical analyzers 32, 38, and 42 for a test that has reached its maximum limit. When a Precision QC is delivered to an clinical analyzers 32, 38, and 42 only tests that have reached their appropriate limit will be scheduled.

It is important that the sample handling worksystem 10 plans the QC material and patient sample delivery timing to minimize disruption to patient sample processing. This will require the sample handling worksystem 10 to place available material on the track for transport before the actual QC expiration to insure the material will arrive exactly when needed.

This look-ahead functionality needs to also be used to alert the user to QC material needs. The system should be able to predict that QC material will be needed based on test requests of on-line samples. Typically, one of the following situations will exist:

a) Precision QC material available, which occurs if the on-line Precision QC material will be appropriately routed to the analyzer(s) that require it.

b) Precision QC material partially available (partial expiration), which occurs if the on-line Precision QC material will be appropriately routed to the analyzer(s) that require it.

c) If QC was scheduled for a test that has exceed the viability limit it will not be run and instead an error message will be generated to indicate that no QC material for that test is available. This should not affect the QC testing of any remaining viable tests.

d) Precision QC material NOT available, which occurs if QC is scheduled for unavailable QC material an error message will be generated to indicate that no QC material is available for the requested test(s).

e) More than One viable QC Level available, which occurs if more than one QC level is being utilized for QC then the sample handling worksystem 10 will either route material for all QC levels each time QC needs to be performed or alternate delivery among the QC levels on-line based on user setup.

f) More then one viable QC material available, which occurs if more than one viable QC material can be used for the QC of an analyte then the sample handling worksystem 10 will route the material having the closest expiration to analyzer(s) that require it.

2. No QC Storage Space Available

If the QC storage lane has been undefined, is currently full of QC materials or has no rack present when a QC material needs a storage location the system will produce a warning message indicating the problem. The QC material will be allowed to take "n" laps on the track before having the QC material placed in the Priority Output rack with an automation error declared.

3. Clinical Analyzers 32, 38, and 42 Precision QC Result Rejected

Precision QC results are rejected when they fail the QC acceptance rule(s) or are manually rejected by the operator. Only one of the following two may exist:

a) Rule Based rejection, which occurs if the rules configured during QC setup are applied to the Precision QC result. If any rule fails the Precision QC is rejected.

b) User Entered rejection, which occurs when QC acceptance is set to manual the operator must manually accept or reject the Precision QC results. The operator, however, has the ability to reject the QC results at any time. If the system automatically accepted the results or all rules passed and the results were accepted the operator still has the ability to manually reject the QC results.

4. Clinical Analyzers 32, 38, and 42 Precision QC Result Accepted

Precision QC results are accepted automatically when they are run, when they pass the QC acceptance rule(s) or are manually accepted by the operator as determined by the "Precision QC acceptance" selection in the QC—Scheduling Rules setup screen. Typically, one of the following three situations will exist:

a) Automatic acceptance, which occurs if "Auto" was selected, every time the Precision QC is run for a test it will be accepted.

b) Rule Based acceptance, which occurs if "Rule" was selected, every time the Precision QC is run for a test it will be analyzed based on the rules defined for QC acceptance. If all rules pass, the Precision QC for the test will be accepted, otherwise it will be rejected.

c) User Entered acceptance, which occurs if "Manual" was selected, every time the Precision QC Sample is run for a test it will remain in the pending state until the operator either accepts or rejects the result.

5. Clinical Analyzers 32, 38, and 42 Precision QC Result Pending

Whenever a QC result is pending (clinical analyzers 32, 38, and 42 has sampled QC but has not produced a result) the sample handling worksystem 10 will schedule patient samples based on the QC setup as follows:

a) If STOP was configured, samples with tests where QC results are pending will not be scheduled. The sample handling worksystem 10 will route these tests to other clinical analyzers 32, 38, and 42s or wait for the QC results to be reported and accepted.

b) If CONTINUE was configured, samples with tests where QC results are pending will be scheduled normally.

6. QC Routing to Clinical Analyzers 32, 38, and 42s with no Inventory If the clinical analyzers 32, 38, and 42 report a zero inventory then a method is out of QC or Calibration. To avoid a QC routing deadlock the sample handling worksystem 10 should send QC material to clinical analyzers 32, 38, and 42 without regard for inventory levels.

7. Reserved QC Pallets to Prevent Deadlock

The system needs to plan and allocate pallet transport of QC material to prevent delivery deadlocks. As each QC material need is developed a track pallet should be allocated. There can be no system state that causes a deadlock (i.e. cannot run patient sample because QC not run & cannot run QC because no pallets available due to patient sample backup).

8. On-line/Off-line of CAL/QC System

The Calibration subsystem and the QC subsystem should be able to be placed on-line or off-line via the Maintenance/System screen. If either of these subsystems are off-line no messages or scheduling/analysis features are to be performed.

Assay Defined Rules

Assay defined rules are requirements placed upon QC/CAL condition of an analyzer 32, 38, or 42 for specific individual assays. These rules specify conditions such as:

1. For assays belonging to a first group of assays for which a heightened level of precision is required in order to correctly diagnose a patient's health, it is required that QC/CAL be conducted using Precision QC materials.

2. For assays belonging to a defined subset of the first group of assays, it is required that QC/CAL be conducted using Precision QC materials which are dated more than a prescribed time before the expiration date of the Precision QC materials.

3. For assays belonging to a defined subset of the first group of assays, it is required that QC/CAL results using Precision QC materials fall within a prescribed value of the label value entered for the Precision QC materials.

4. For assays belonging to a second group of assays for which a normal level of precision is required in order to correctly diagnose a patient's health, it is required that QC/CAL be conducted using Accuracy QC materials.

5. Assay must be performed on an analyzer where Precision QC has been successfully completed and:
   QC results were within +/−5% of label value, or
   QC results were within +/−25% of label value.

6. Assay must be performed on an analyzer where Precision QC has been successfully completed and:
   QC was performed "X" days before QC material was to expire, or
   QC was performed before QC material was to expire.

7. Assay must be performed on an analyzer where Precision QC has been successfully completed and:
   QC was performed less than "X" days or "Y" hours before assay is to be run, or
   QC was performed less than "Z" days or "W" hours before assay is to be run, or
   QC was performed before QC material was to expire.

8. Assay must be performed on an analyzer where Precision QC has been successfully completed and:
   a fresh (previously unused) cuvette must be employed, or
   the assay cannot be performed in a washed (previously used) cuvette in which any assay in the following group has been immediately previously performed, the group comprising assay A, B, C, and D, or
   the assay may be performed in a washed (previously used) cuvette regardless of what assay was immediately previously performed therein.
   All of the above for an assay that can be performed on an analyzer where Precision QC or Accuracy QC has been successfully completed.

9. Assay is preferred to be performed on an analyzer where Precision QC has been successfully completed; however, if Precision QC is not available, the assay may be run on an analyzer in which Accuracy QC has been successfully completed (and so reported with test results), and:
   QC results were within +/−5% of label value; or
   QC results were within +/−25% of label value; or QC was performed "X" days before QC material was to expire; or QC was performed before QC material was to expire; or QC was performed less than "X" days or "Y" hours before assay is to be run; or QC was performed less than "Z" days or "W" hours before assay is to be run; or QC was performed before QC material was to expire.

10. If the results of an assay are more than Z % outside normal range and the assay was performed on a analyzer for which Precision QC was successfully completed, then re-run the assay on an analyzer for which Accuracy QC was successfully completed, and so note in the test report.

11. Some reflux testing rules, like a) assay X must be run if the results for assay Y were out of normal range, or b) assay X and Z must be run if the results for assay Y were out of normal range Analyzer Operational Status Analyzer defined rules are requirements placed upon analyzer 32, 38, or 42 in order to assure reliable and accurate operation. These rules specify conditions such as, but not limited to:

1. Prior analysis of Precision QC materials confirms the following:

Most recent result less than three times the standard deviation from the arithmetic mean.

Seven most recent results not all above arithmetic mean.

Seven most recent results not all below arithmetic mean.

Seven most recent results do not show an upward trend.

Seven most recent results do not show a downward trend.

2. Prior analysis of Accuracy QC materials confirms the following:

Most recent result less than five times the standard deviation from the arithmetic mean.

Three most recent results not all above arithmetic mean.

Three most recent results not all below arithmetic mean.

Three most recent results do not show an upward trend.

Three most recent results do not show a downward trend.

3. Sufficient reagents are available on-board to conduct a specified assay of an incoming sample and these reagents are not on-board beyond the expiration dates of the reagents.

4. Incoming sample containers 20 containing samples to be assayed have a quality is acceptable for processing, being free of clots, fibrin and other impurities that may affect metering fluids through the analyzer.

5. Incoming sample containers 20 containing samples to be assayed have been correctly centrifuged and/or de-capped as required by automated centrifuge 24 and automated tube de-capper 30.

6. Incoming sample containers 20 containing samples to be assayed have sufficient sample liquids therein to ensure there is sufficient sample for the requested assays.

7. In the event that incoming sample containers 20 containing samples to be assayed are pediatric sample containers 20, the orientation of a pediatric sample container 20 is confirmed before sample is aspirated therefrom.

EXAMPLE

The following Example is presented a non-limiting illustration of the present method for automatically ensuring that assays specified to be conducted on samples in incoming sample containers 20 are performed only on an analyzer 32, 38, and 42 which is in compliance with the set of assay defined rules associated with the assays to be conducted.

Twelve sample containers 20 originally contained in a sample rack 18 are individually removed by sample tube loading/unloading station 16 from sample rack 18 and placed into individual sample tube carriers 22. Based upon sample container identification indicia, such as a bar code, conveyor track 14 is controlled by CPU 15 and laboratory LIS to transport individual sample tube containers 20 as required by the prescribed assay(s) to be conducted on the sample therein to an automated centrifuge 24 and/or to an automated tube de-capper 30 for automatically removing caps from capped sample containers 20.

CPU 15 and/or laboratory LIS compare the assays to be conducted for each of the samples contained within sample tube containers 20 with a set of assay defined rules with the current operational status of analyzers 32, 38, and 42 so as to determine which sample tube containers 20 should be transported by conveyor track 14 to which analyzer 32, 38, or 42 whereat the assays to be conducted may be completed in compliance with the assay defined rules. For instance, a sample rack 18 contains the following sample tube containers 20:

1. Three sample tube carriers 22a, 22b, and 22c carry patient samples for which assays to be conducted require that a successful Precision QC Acceptance has been accomplished within the previous 2 hours;

2. Three sample tube carriers 22d, 22e, and 22f carry patient sample for which assays to be conducted require that a successful Precision QC Acceptance has been accomplished within the previous 8 hours;

3. Two sample tube carriers 22g and 22h carry patient sample for which assays to be conducted require that the assay must be performed on an analyzer where Precision QC has been successfully completed and QC results were within +/−5% of label value;

4. Three sample tube carriers 22i, 22j and 22k carry patient sample for which assays to be conducted require that the assay must be performed on an analyzer where QC/CAL has been successfully conducted before QC material was to expire using Accuracy QC materials;

5. One sample tube carriers 22m carry patients sample for which an assay to be conducted requires a fresh to be employed; and, 6. One sample tube carrier 22n contains patient sample for which assays to be conducted require that the assay must be performed on an analyzer where Accuracy QC has been successfully completed and QC results were within +/−25% of label value.

In this instance CPU 15 and/or laboratory LIS compare these six different assay defined rules with the current operational status of analyzers 32, 38, and 42, determine, for instance, that:

Analyzer 32 is in compliance with the assay defined rules for patient sample carried by sample tube carriers 22a, 22b, and 22c and for sample tube carrierr 22n;

Analyzer 38 is in compliance with the assay defined rules for patient sample carried by sample tube carriers 22i, 22j and 22k;

Analyzer 42 is in compliance with the assay defined rules for patient sample carried by sample tube carriers 22d, 22e, and 22f and for sample tube carrier 22m; and No analyzer is in compliance with the assay defined rules for patient sample carried by sample tube carriers 22g and 22h.

Figure 7:
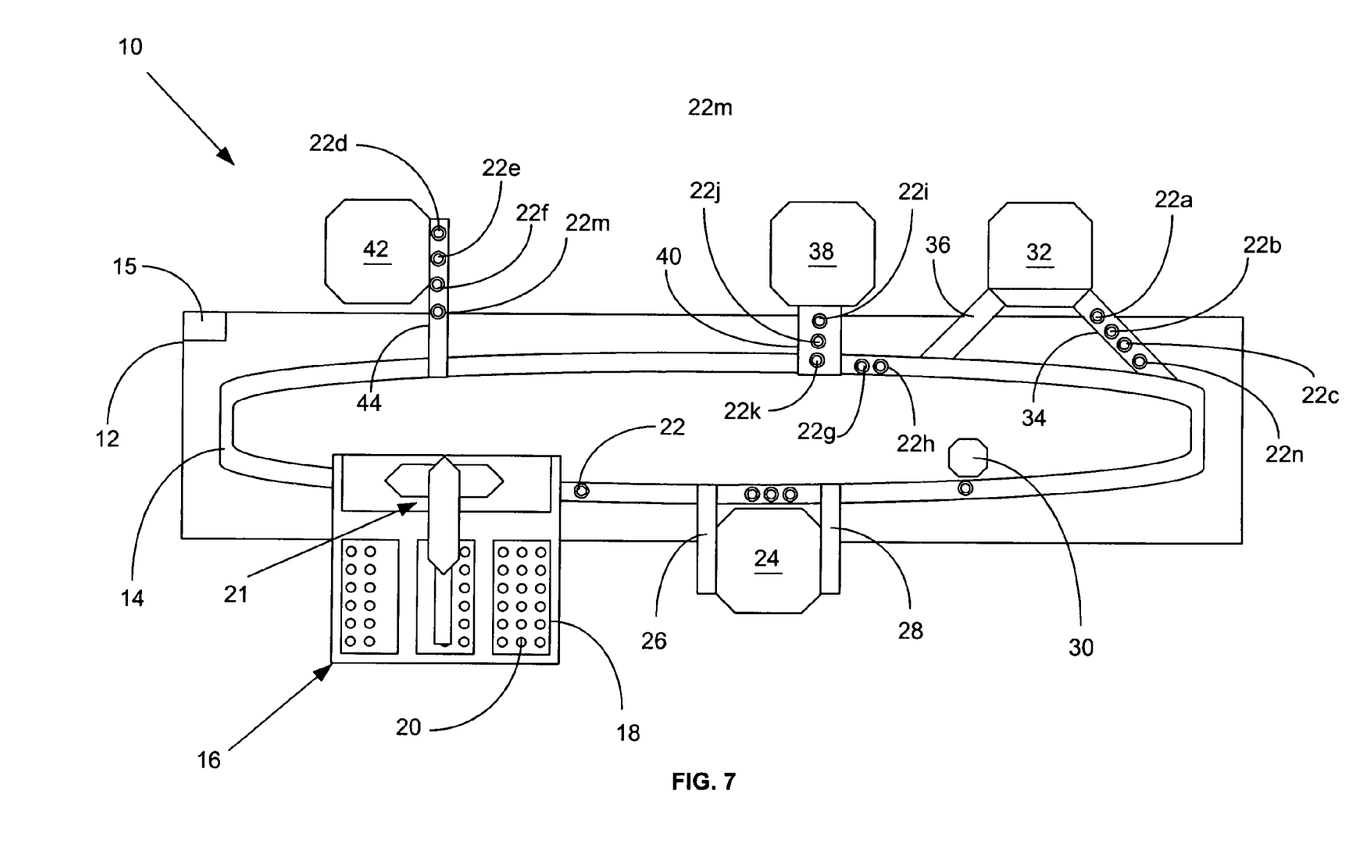

Clearly, CPU 15 is able to operate sample handling worksystem 10 like seen in FIG. 7 so that sample tube carriers 22a, 22b, and 22c and for sample tube carrier 22n are transported by conveyor track 14 to analyzer 32, so that sample tube carriers 22i, 22j and 22k are transported by conveyor track 14 to analyzer 38, and 22d, 22e, and 22f and for sample tube carrier 22m are transported by conveyor track 14 to analyzer 42 whereat the assays to be conducted may be completed in compliance with the assay defined rules.

In contrast, however, in this example, none of the analyzers 32, 38, or 42 are in an operational status so that sample in sample tube carriers 22g and 22h may be assayed on an analyzer where Precision QC has been successfully completed and QC results were within +/−5% of label value. In such an instance, sample handling worksystem 10 is automatically operated such that:

1. If Precision QC material is available within the on-board storage of materials within sample handling worksystem 10, CPU 15 will operate sample handling worksystem 10 so such Precision QC material will be transported by conveyor track 14 to analyzer 38, for example, and a Precision calibration process conducted. Once the Precision calibration process is completed, the results will be compared to label value and either:

the QC results are within +/−5% of label value, in which instance, CPU 15 will operate sample handling worksystem 10 so that sample in sample tube carriers 22g and 22h will be transported by conveyor track 14 to analyzer 38 and the assay automatically conducted thereon, or the QC results are not within +/−5% of label value, in which instance, CPU 15 will operate sample handling worksystem 10 so that either:

1. the assay will not be conducted and an error message will be displayed by CPU 15 so that operator assistance may be obtained, or
    2. CPU 15 will operate sample handling worksystem 10 so that sample in sample tube carriers 22g and 22h will be transported by conveyor track 14 to analyzer 38, the assay automatically conducted thereon, and the results will be reported to the LIS along with a notation that the assay was performed on an analyzer not in compliance with the assay defined rules. Note that this particular situation, wherein the assay was performed on an analyzer not in compliance with the assay defined rules, is only possible if User Defined Rules as described herein, permit such an action.

2. If Precision QC material is no available within the on-board storage of materials within sample handling worksystem 10, CPU 15 will generate an error message to indicate that no QC material is available for the requested test(s) so that operator assistance may be obtained.

Those skilled in the art will appreciate that the embodiments of the invention disclosed herein are illustrative of the principles of the invention and that other modifications may be employed which are still within the scope of the invention. For example, obvious variants of the invention would include in the event that a STAT or emergency sample require immediate assaying for an assay having assay defined rules that require the assay to be performed on an analyzer where Accuracy QC has been successfully completed and QC results were within +/−25% of label value, and none of analyzers 32, 38, or 42 has a analyzer operational status in compliance with such an Accuracy QC result, then the STAT sample could be immediately processed upon an analyzer 32, 38, or 42 for which a corresponding Accuracy QC has been successfully completed and QC results were within +/−5% of label value. Accordingly, the present invention is not limited to those embodiments precisely shown and described in the specification but only by the following claims.

What is claimed is:

1. A method for automatically operating a sample handling system including a conveyor controlled in cooperation with several analysis pre-treatment devices and analyzers adapted to conduct assays on a number of patient samples, the method comprising:

assigning to each assay assay-specific required levels of calibration and quality control conditions;

comparing the assays to be conducted with calibration and quality control conditions on each analyzer;

subdividing the analyzers into a first group of analyzers with calibration and quality control conditions in compliance with the assay-specific required levels of calibration and quality control conditions and into a second group which are not in compliance with the assay-specific required levels of calibration and quality control conditions; and then, either operating the sample handling system so as to supply patient samples to analyzers within the first group of analyzers; or, operating the sample handling system so as to bring at least one analyzer within the second group of analyzers into compliance with the assay-specific required levels of calibration and quality control conditions and then supplying patient samples to analyzers in the second group, wherein bringing at least one analyzer within the second group of analyzers into compliance with the assay-specific required levels of calibration and quality control conditions comprises supplying calibration and quality control solutions to said analyzer and conducting a calibration process.

2. The method of claim 1 wherein the assay-specific required levels of calibration and quality control conditions include quality control results being within predetermined ranges or dates.

3. The method of claim 1 wherein the assay-specific required levels of calibration and quality control conditions include quality control results being within predetermined standard deviations.

* * * * *